United States Patent [19]

Ensminger

[11] Patent Number: 5,352,204
[45] Date of Patent: Oct. 4, 1994

[54] IMPLANTABLE ACCESS DEVICES

[76] Inventor: William D. Ensminger, 2770 Parkridge Dr., Ann Arbor, Mich. 48103

[21] Appl. No.: 128,841

[22] Filed: Sep. 29, 1993

Related U.S. Application Data

[60] Division of Ser. No. 940,626, Sep. 4, 1992, Pat. No. 5,263,930, which is a continuation-in-part of Ser. No. 818,626, Jan. 10, 1992, Pat. No. 5,226,879, which is a continuation-in-part of Ser. No. 654,661, Feb. 15, 1991, Pat. No. 5,180,365, which is a continuation-in-part of Ser. No. 539,793, Jun. 18, 1990, Pat. No. 5,053,013, which is a continuation-in-part of Ser. No. 487,541, Mar. 1, 1990, Pat. No. 5,057,084.

[51] Int. Cl.$^5$ .............................................. A61M 11/00
[52] U.S. Cl. ..................................... 604/93; 604/175; 604/190
[58] Field of Search ................... 604/93, 190, 167, 175

[56] References Cited

U.S. PATENT DOCUMENTS

| | | |
|---|---|---|
| 3,288,137 | 1/1964 | Lund . |
| 3,402,710 | 9/1968 | Paleschuck . |
| 3,565,078 | 2/1971 | Vailiancourt et al. . |
| 3,699,956 | 10/1972 | Kitrilakis et al. . |
| 4,181,132 | 1/1980 | Parks . |
| 4,190,040 | 2/1980 | Schulte . |
| 4,230,109 | 10/1980 | Geiss . |
| 4,256,102 | 3/1981 | Monaco . |
| 4,387,879 | 6/1983 | Tauschinski . |
| 4,405,320 | 9/1983 | Cracauer et al. . |
| 4,425,119 | 1/1984 | Berglund . |
| 4,430,081 | 2/1984 | Timmermans . |
| 4,439,188 | 3/1984 | Dennehey et al. . |
| 4,447,237 | 5/1984 | Frisch et al. . |
| 4,464,178 | 10/1984 | Dalton . |
| 4,490,137 | 12/1984 | Moukheibir . |
| 4,491,126 | 1/1985 | Cullor . |
| 4,543,088 | 9/1985 | Bootman et al. . |
| 4,547,194 | 10/1985 | Moorehead . |
| 4,569,675 | 2/1986 | Prosl et al. . |
| 4,578,061 | 3/1986 | Lemelson . |
| 4,578,063 | 3/1986 | Inmann et al. . |
| 4,581,020 | 4/1986 | Mittleman . |
| 4,623,329 | 11/1986 | Drobish et al. . |
| 4,634,422 | 1/1987 | Kantrowitz et al. . |
| 4,645,495 | 2/1987 | Vaillancourt . |
| 4,650,473 | 3/1987 | Bartholomew et al. . |
| 4,673,394 | 6/1987 | Fenton, Jr. et al. . |
| 4,682,981 | 7/1987 | Suzuki et al. . |
| 4,692,146 | 9/1987 | Hilger . |
| 4,695,273 | 9/1987 | Brown . |
| 4,704,103 | 11/1987 | Stober et al. . |
| 4,710,167 | 12/1987 | Lazorthes . |
| 4,710,174 | 12/1987 | Moden et al. . |
| 4,712,583 | 12/1987 | Pelmulder et al. . |
| 4,781,680 | 11/1988 | Redmond et al. . |

(List continued on next page.)

FOREIGN PATENT DOCUMENTS

| | | |
|---|---|---|
| 0119596 | 3/1984 | European Pat. Off. . |
| 134745 | 8/1984 | European Pat. Off. . |
| 3528878 | 2/1987 | Fed. Rep. of Germany . |

OTHER PUBLICATIONS

Rational Drug Therapy, May 1988, vol. 22, No. 5, William D. Ensminger M.D. and Ira S. Wollner, M.D.

*Primary Examiner*—John D. Yasko
*Attorney, Agent, or Firm*—Harness, Dickey & Pierce

[57] ABSTRACT

One aspect of the present invention is an implantable patient access port which provides a percutaneous route for access using an external filament such as an external catheter needle, wire or optical fiber. The access port incorporates an internal reservoir for the retention of an antibacterial fluid and further includes a means for refilling the fluid chamber. Refilling is accomplished through providing a separate fluid reservoir within the housing and further through the provision of a barrier which can be penetrated using a needle. Another aspect of the invention is the provision of a blood check device which prevents migration of red blood cells from a percutaneously placed accessed catheter outside of the patient. The device includes a filter media element and connector for permitting in-line placement of the blood check in the access catheter.

4 Claims, 3 Drawing Sheets

U.S. PATENT DOCUMENTS

| | | |
|---|---|---|
| 4,781,693 | 11/1988 | Martinez et al. . |
| 4,781,695 | 11/1988 | Dalton . |
| 4,790,826 | 12/1988 | Elftman . |
| 4,802,885 | 2/1989 | Weeks et al. .......................... 604/93 |
| 4,810,241 | 3/1989 | Rogers . |
| 4,832,054 | 5/1989 | Bark ................................... 604/93 X |
| 4,842,591 | 6/1989 | Luther . |
| 4,857,053 | 8/1989 | Dalton . |
| 4,857,062 | 8/1989 | Russell . |
| 4,886,501 | 12/1989 | Johnston et al. . |
| 4,929,235 | 5/1990 | Merry et al. . |
| 4,936,831 | 6/1990 | Jaehrling et al. ................... 604/190 |

IMPLANTABLE ACCESS DEVICES

CROSS REFERENCE TO RELATED APPLICATIONS

This is a division of U.S. patent application Ser. No. 07/940,626, filed Sep. 4, 1992 now U.S. Pat. No. 5,263,930 and entitled: Implantable Access Devices which, is a continuation-in-part of U.S. application Ser. No. 818,626 filed on Jan. 10, 1992 now U.S. Pat. No. 5,226,879, entitled "Implantable Infusion Device" which is a continuation-in-part of U.S. application Ser. No. 654,661, filed on Feb. 15, 1991, now U.S. Pat. No. 5,180,365 which is a continuation-in-part of U.S. application Ser. No. 539,793 filed on Jun. 18, 1990 now issued as U.S. Pat. No. 5,053,013, which is a continuation-in-part of U.S. patent Ser. No. 487,541 filed on Mar. 1, 1990 now issued as U.S. Pat. No. 5,057,084, the disclosure of which are hereby incorporated by reference and are collectively referred to as the related applications.

FIELD OF THE INVENTION

This invention relates to devices for introducing a filament, such as a catheter, into a patient for infusing a therapeutic agent to a desired site or withdrawing a fluid from the patient. More particularly, the invention relates to an access port which is implanted such that no portion is transcutaneous. The access port is subcutaneous but designed so as to facilitate repeated access by the percutaneous route.

BACKGROUND AND SUMMARY OF THE INVENTION

In current human and animal medical practice, there are numerous instances where therapeutic agents must be delivered to a specific organ or a tissue within the body. An example is the infusion of chemotherapy into a central vein on a recurring basis over a lengthy treatment period for widespread sites of malignant tumor. Without an access device for intravenous drug infusion, multiple vein punctures over a lengthy period would result in progressive thrombosis, venous sclerosis, and destruction of small diameter peripheral vessels. In other cases, it may be desirable to infuse chemotherapy to a localized malignant tumor site. It may be difficult or impossible to deliver an agent specifically to such a site on a regular repetitive basis without surgically implanting an access system. Similarly, repeated arterial access is occasionally needed for injection of an X-ray dye or contrast agent for diagnostic purposes. In other situations, there is a need to repetitively remove a body fluid for analysis from a remote body site. Finally, sensing and physiological measuring devices incorporated into small diameter catheters and optical fibers are increasingly being utilized for monitoring body processes and could be more easily implemented through a properly designed access device with an adequate internal diameter.

In prior medical practice, percutaneous catheters have been used to provide vascular or organ access for drug therapy or the withdrawal of body fluids. Although such systems generally perform in a satisfactory manner, numerous problems were presented by such therapy approaches, including the substantial care requirements of the patients, e.g. dressing changes with sterile techniques, a significant rate of infection of the catheter because of its transcutaneous position, and a high rate of venous thrombosis, particularly if the catheter was located within an extremity vein.

Implantable infusion devices or "ports" have recently become available and represent a significant advance over transcutaneous catheters. Presently available infusion ports have a number of common fundamental design features. The ports themselves comprise a housing which forms a reservoir that can be constructed from a variety of plastic or metal materials. A surface of the reservoir is enclosed by a high-density, self-sealing septum, typically made of silicone rubber. Connected to the port housing is an implanted catheter which communicates with a vein or other site within the patient where the infusion of therapeutic agents is desired. Implantation of such devices generally proceeds by making a small subcutaneous pocket in an appropriate area of the patient under local anesthesia. The implanted catheter is tunnelled to the desired infusion site. When the care provider desires to infuse or remove materials through the port, a hypodermic needle is used which pierces the skin over the infusion port and is placed into the port.

Although the presently available implantable infusion ports generally operate in a satisfactory manner, they have a number of shortcomings. Since these devices rely on a compressed rubber septum for sealing and since large diameter needles can seriously damage the septum, there are limitations in the diameter of needles which can be used to penetrate the septum. These diameter limitations severely restrict the opportunities provided by the port. In cases where it is desirable to infuse drugs using a flexible external catheter, the catheter must be fed through the needle that penetrates the septum. Such catheters have an extremely small inside diameter and, therefore, impose severe limitations on fluid flow rate and limit the types of fibers which can be introduced, During prolonged infusion using a conventional port, the infusion needle is taped to the patient's skin to hold it in position. Conventional ports do not allow the needle to penetrate deeply into the port. Because of this, a small displacement of the needle can cause it to be pulled from the port. In cases where locally toxic materials are being infused, extravasation of such materials can cause local tissue damage which may require corrective surgery such as skin grafting or removal of tissue.

Presently available implantable drug infusion devices also have a significant size to provide an acceptable target surface area for the care provider who must locate the port and penetrate the septum with a needle. The port housing becomes bulky as the septum size increases since structure is required to maintain the septum in compression to provide self-sealing after the needle is removed. Moreover, presently available infusion ports are difficult to clear if thrombosis occurs within the port or within the implanted catheter since it is difficult, if not impossible, to feed a cleaning wire through the penetrating hypodermic needle in a manner which will clear the infusion device and the internal catheter. Present infusion ports also have a retained volume beneath the self-sealing septum which increases the volume of drug which must be administered to enable a desired quantity to reach the infusion site. This retained volume also poses problems when a care provider desires to successively deliver multiple drugs to the same infusion site which are incompatible when mixed. Additionally, when it is desired to withdraw blood through the port, the retained volume of the prior art infusion ports comprises an area where blood clotting can occur, thus interfering with future access to the site. And finally, for present infusion ports, there is a risk that the care provider attempting to pierce the port septum will not properly enter it, leading to the possibility of extravasation which can cause significant undesirable consequences as mentioned above.

The present invention relates to a family of implantable access ports which provide numerous enhancements over prior art devices. In accordance with this invention, an access port is provided which incorporates the funnel-shaped entrance orifice which narrows down to a reduced diameter passageway. Positioned within the passageway is an "articulating catheter valve or articulating valve", such as a multi-element leaflet valve assembly. The exit passageway of the port is connected to an implanted catheter which communicates with a desired site in the body.

One of the embodiments encompassed by the present application relates to an access port having a chamber for the retention of an antimicrobial or antibacterial fluid which aides in the prevention of infection in the area of the access port and particularly along the route of the percutaneously placed filament. Whenever a percutaneous route is provided the risk of infection is present. In the access port in accordance with this invention, the antibacterial solution can be made to slowly diffuse from the access port as an effective preventive measure against infection. In addition, the antibacterial fluid is permitted to coat the percutaneous filament as it is inserted and withdrawn from the port. The access port of this invention further provides a means for replenishing the antibacterial fluid chamber after the port is placed through a transcutaneous refilling instrument, through provision of a separate fluid reservoir, or both.

Access ports in accordance with the present invention provide a large diameter access pathway to a remote site within the patient. In some patient treatment procedures prolonged infusions take place. Since the flow rate may be very low, there is a possibility that blood can backflow through the percutaneous catheter through the process of diffusion or under the influence of gravity. Patients can be traumatized or led to believe that the infusion system is operating improperly when blood is seen in the external catheter. As a means of precluded such reverse flow of blood through an external catheter, a blood stop device is provided in accordance with one aspect of this invention which is connected in-line with the external catheter close to the location of the access port. The device uses a filter media element having a filtration capability which traps red blood cells backflowing through the external catheter. Therefore, any red blood cells diffusing into the external catheter collect on a surface of the filter media element as opposed to traveling further in the external catheter. The blood stop of this invention can be used in connection with the various access ports described herein or in the related applications.

Additional benefits and advantages of the present invention will become apparent to those skilled in the art to which this invention relates from the subsequent description of the preferred embodiments and the appended claims, taken in conjunction with the accompanying drawings.

DETAILED DESCRIPTION OF THE INVENTION

Figure 1:
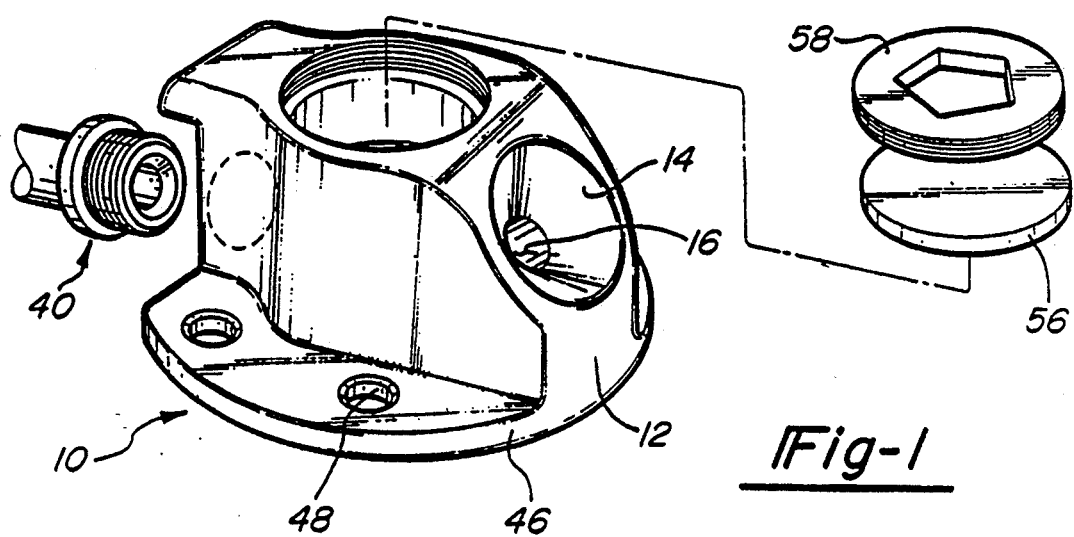
FIG. 1 is an exploded pictorial view of an access port incorporating an antibacterial fluid reservoir in accordance with one aspect of this invention.
Figure 2:
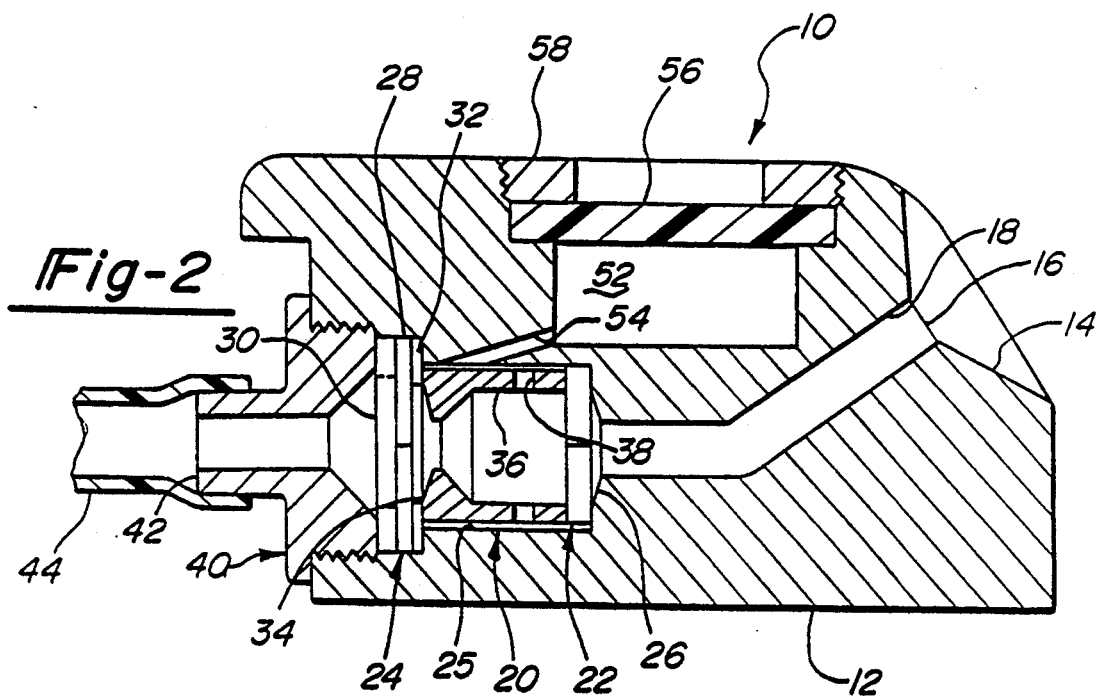
FIG. 2 is a cross-sectional view of the access port of FIG. 1.

An access port in accordance with a first embodiment of this invention is shown in FIG. 1 and is generally designated there by reference number 10. Access port housing 12 forms a funnel shaped entrance orifice 14 which narrows down to a focus area 16 and to internal passageway 18. Passageway 18 may form a curved path as shown best in FIG. 2 which prevents a rigid accessing instrument from passing completely through the passageway and thus acts as a "needle stop" as described in the related applications.

As is the case of each member of the family of implantable access ports described herein and in the related applications, housing 12 forms a mounting surface for supporting the device subcutaneously. In port 10 support is provided by a radially extending flange 46 at the base of housing 12. Flange 46 can be provided with mounting holes 48 which enable sutures or surgical staples to securely mount housing 12 to appropriate subcutaneous tissue. Even when such fasteners are not used, holes 48 serve to stabilize the port as tissue will tend to form in the holes.

Passageway forms an antibacterial fluid chamber 20 inside housing 12. Fluid chamber 20 is provided for the retention of an antibacterial fluid (or anti-microbial fluid, with these terms being used interchangeably) and is bounded by a pair of valves 22 and 24. Valve 22 is a leaflet type valve comprised of a single flat disk of resilient material such as silicone rubber which is cut to form two or more deflectable leaves. Valve 24 is also a leaflet type valve, but is comprised of a multiple leaflet stack having a pair of disks of resilient material 28 and 30, each having one or more cuts across their surface thus each forming two or more deflectable leaves. As explained in the related applications, the cuts that define the leaves of stacked together disks 28 and 30 are rotationally indexed such that they are not in registry and preferable to the maximum extent possible, which aides in providing fluid sealing. Valve 24 further incorporates a donut or ring valve element 32 which is simply a flat disk of resilient material having a circular central aperture 34. Aperture 34 is dimensioned to seal against an external filament which is introduced into access port 10, as will be described in more detail. Valve elements 5 disks 28 and 30, and the element comprising valve 22 can be made of surgical silicone rubber having a hardness number of 27, Shore A, and a thickness of 0.040 inches. Ring valve element 32 can also be made of surgical silicone rubber having a hardness of 50, Shore A, and a thickness of 0.040 inches.

Valves 22 and 24 are supported within fluid chamber 20 by hollow bushing 36 which has perimeter flow passages. 38. An annular clearance space 25 is provided within fluid chamber 20 around bushing 36. Valves 22 and 24, and bushing 36 are maintained within housing 12 through the clamping action of outlet plug 40 which is threaded or press-fit into housing 12. Outlet plug 40 has an outlet nipple 42 to which implanted catheter 44 is attached. Additional details of valves 22 and 24 and the elements comprising them can be obtained by reference to the related applications.

Fluid chamber 20 provides a volume for the retention of an antibacterial fluid which is intended to aid in the prevention of infection after port 10 is implanted. A design of an implantable port incorporating an antibacterial fluid chamber is described and claimed in related application Ser. No. 487,541, now U.S. Pat. No. 5,057,084. The previously described device, however, did not incorporate a means for enabling the antibacterial fluid chamber to be refilled after implantation of the port. The present embodiment, however, incorporates such features.

Housing 12 forms an internal reservoir chamber 52 which communicates with fluid chamber 20 through passage 54. Reservoir chamber 52 is enclosed by a barrier for enabling refilling, which in this case is a compressed rubber septum 56 which is held in position by threaded mounting ring 58. As will be described in more detail, septum 56 is provided to enable a transcutaneous refilling instrument to be used to replenish the supply of antibacterial fluid within reservoir chamber 52, and therefore fluid chamber 20.

Figure 3:
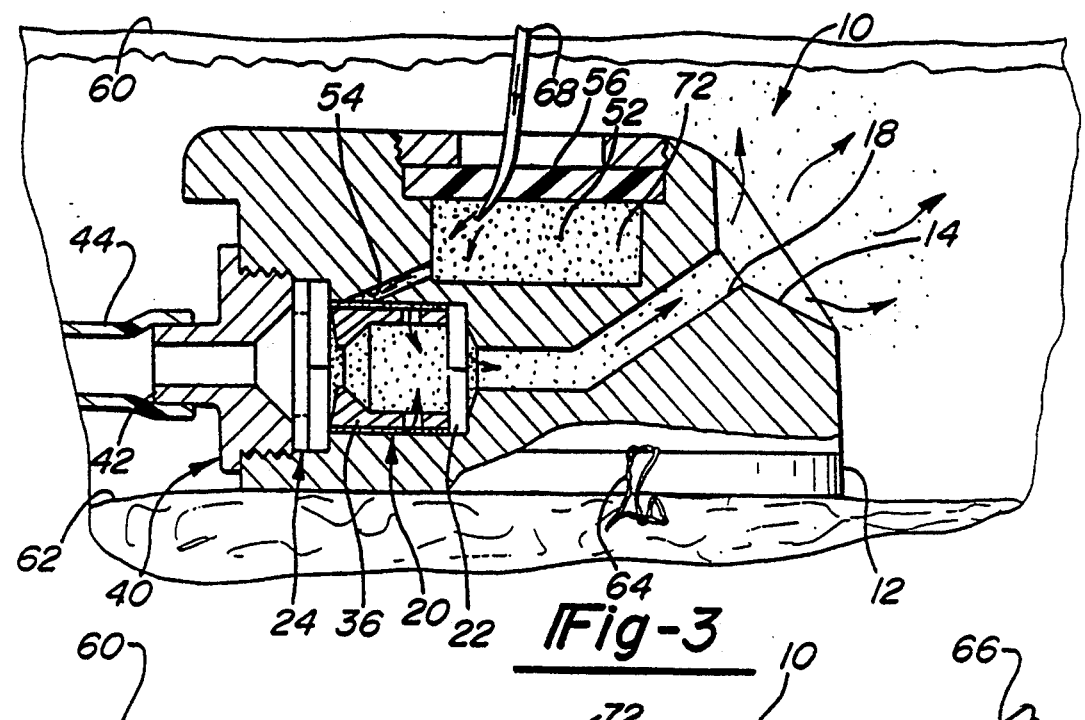
FIG. 3 is a cross-sectional view of the access port shown in FIG. 1 after implantation within a patient and showing the antibacterial fluid reservoir being refilled by a hypodermic needle.
Figure 4:
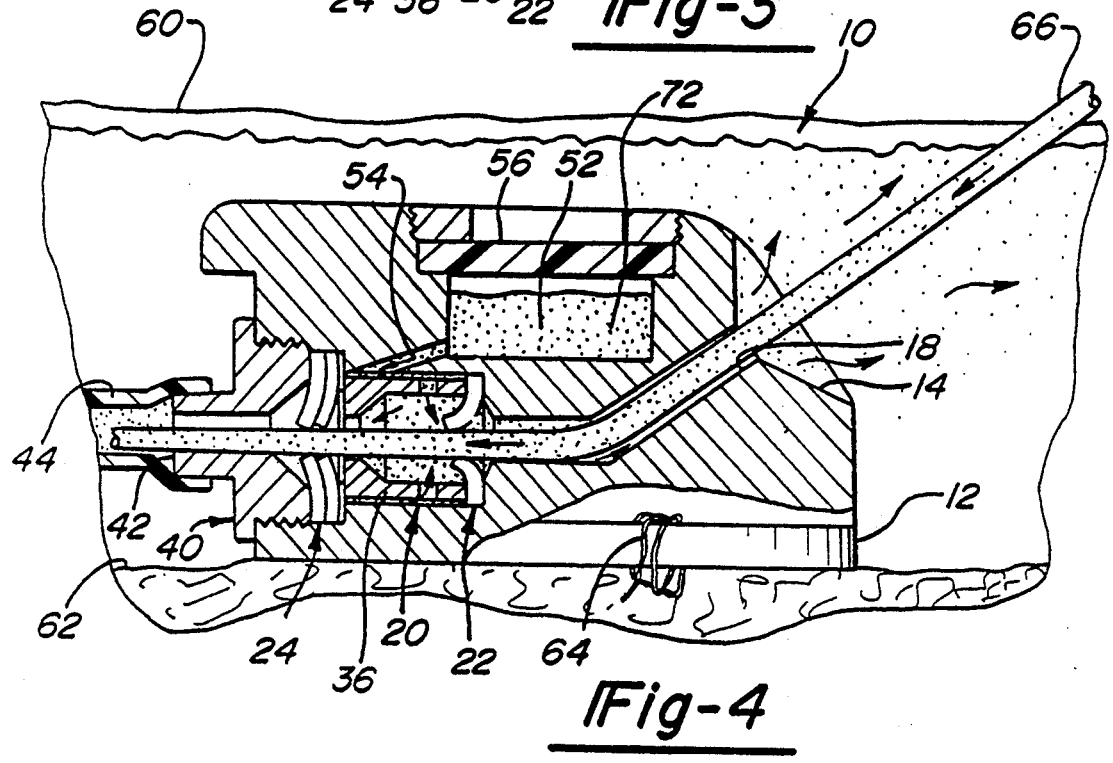
FIG. 4 is a cross-sectional view of the access port shown in FIG. 1 after implantation and showing the diffusion of the retained antibacterial fluid as the device is being accessed by an external filament.

FIGS. 3 and 4 show access port 10 implanted beneath the skin 60 and affixed to fascia tissue 62 using sutures 64. Implanted catheter 44 is tunneled to an appropriate site within the body such as a specific organ, peripheral vein or artery, depending on the medical application. Prior to implantation, reservoir chamber 52 would preferably be filled with a quantity of antibacterial fluid 72. Fluid 72 flows through passage 54 and at least partially fills fluid chamber 20. FIG. 4 illustrates access port 10 being used to provide percutaneous access and showing external filament 66, which can be a catheter, wire, optical fiber or other flexible filament placed through port 10. During insertion and removal of external filament 66, its outer surfaces becomes coated with antibacterial fluid 72 within fluid chamber 20 which provides a barrier against infection along the percutaneous route. The fluid within chamber 20 is replenished due to the volume of material within reservoir chamber 52.

FIG. 3 illustrates refilling of reservoir chamber 52 through the use of a transcutaneous refilling instrument which is shown as a hypodermic needle 68, which is preferably of the non-coring variety or of a small gage (e.g. 26 gage or smaller). After needle 68 penetrates septum 56, a volume antibacterial solution 72 is injected. A sufficient volume of fluid 72 is injected to recharge reservoir chamber 52 and fluid chamber 20, and may also result in some intentional leakage of antibacterial fluid into passageway 18 and in the area surrounding entrance orifice 14 as shown by the arrows in FIG. 3. When antibacterial fluid 72 is infused into reservoir chamber 52 it flows through passage 54 and into clearance space 25 and from there through passages 38 and into the interior of bushing 36. The orientation of passage 54 can intentionally be made such that needle 68 cannot be inserted into fluid chamber 20.

The level of resistance to the flow of fluids across valve 22 and 24-in the normal condition of port 10 when external filament 66 is not present as well as the sealing provided by the valves around the external filament can be of different levels. Valve 22 comprises a single disk element and, therefore, inherently provides a lessor resistance to fluid flow as compared with valve 24 comprised of three elements. Therefore, when fluid 72 is introduced into chamber 20 under pressure during refilling, it tends to "leak" more readily through valve 22, which is advantageous since it provides the intentional leakage of fluid into a region where the risk of infection is high. Moreover, redundancy in fluid resistance is not necessary for valve 22 since an adequate level of fluid resistance through the port is provided by valve 24. Valve 22 also allows antibacterial fluid to cling to filament 66 as it is withdrawn, thus ensuring transfer of the fluid allowing the percutaneous route, where it is needed. Antibacterial fluid is further infused along the percutaneous route due to minor movement of filament 66 which inevitably occurs, resulting in a "milking" action.

Figure 5:
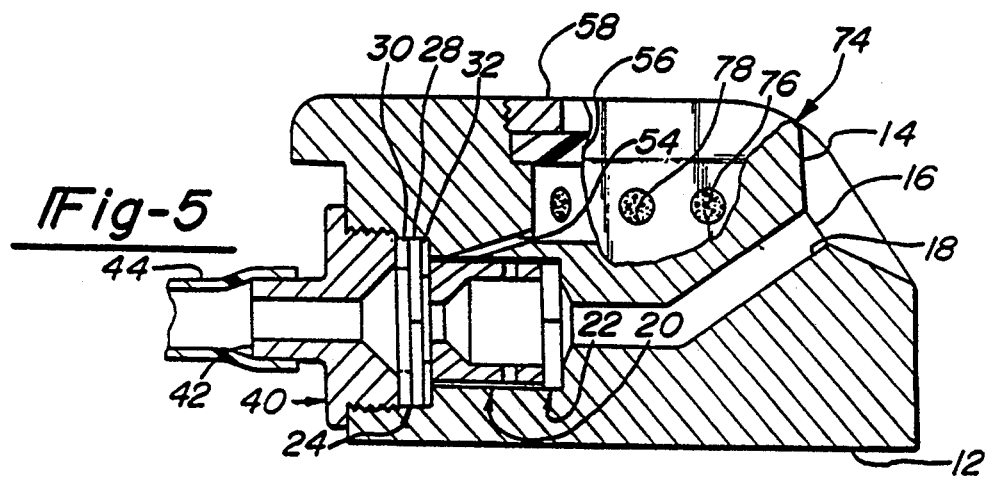
FIG. 5 is a cross-sectional view similar to FIG. 2 but showing an alternate embodiment of the access port shown in FIG. 1.

FIG. 5 discloses an alternate embodiment of access port 10 which is identified by reference number 74. Access port 74 is identical to access port 10 with the exception that passageways 76 are provided through housing 12 and into reservoir chamber 52. Passageways 76 are filled with porous plugs 78 which provide for the slow dispersion of antibacterial fluid 72 within reservoir chamber 52 into the tissue surrounding port 74 for additional resistance to infection.

Figure 6:
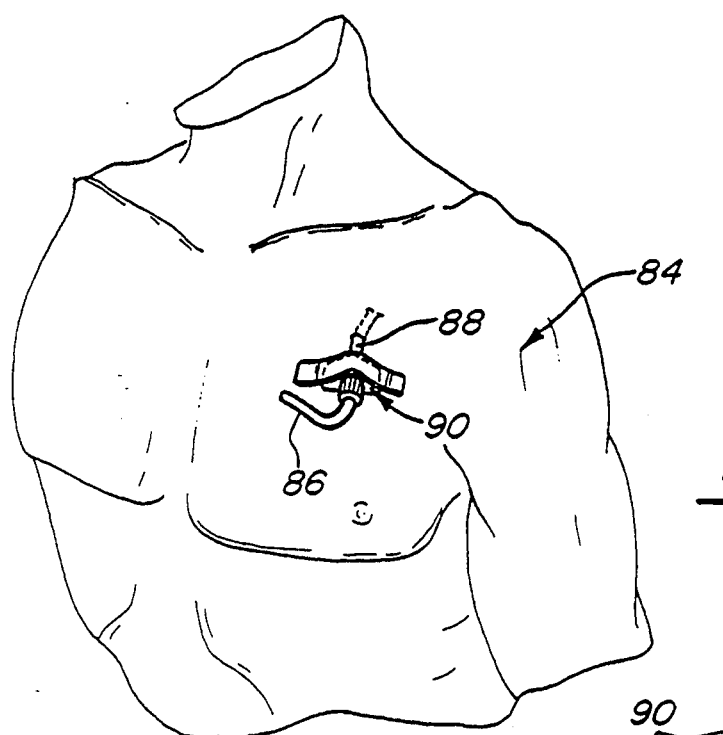
FIG. 6 is a pictorial view of a patient having an implanted access port with a percutaneous access catheter placed for infusion and showing a blood stop device according to another aspect of this invention connected into the access catheter.
Figure 7:
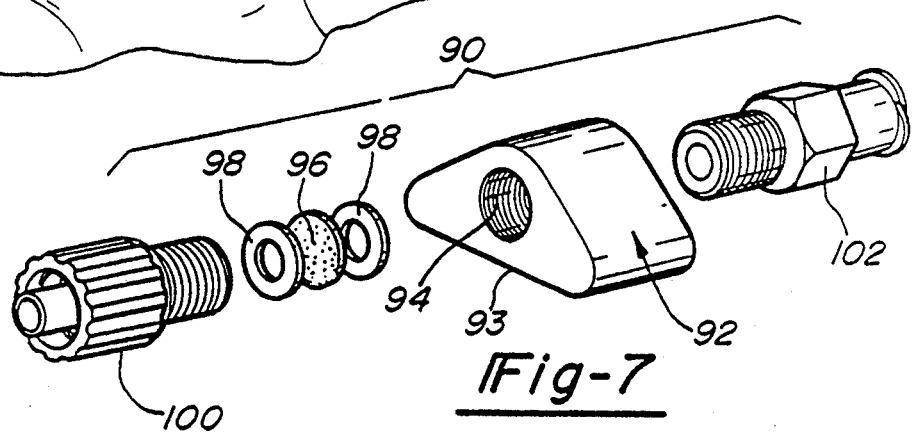
FIG. 7 is an exploded pictorial view of the blood stop device shown in FIG. 6.
Figure 8:
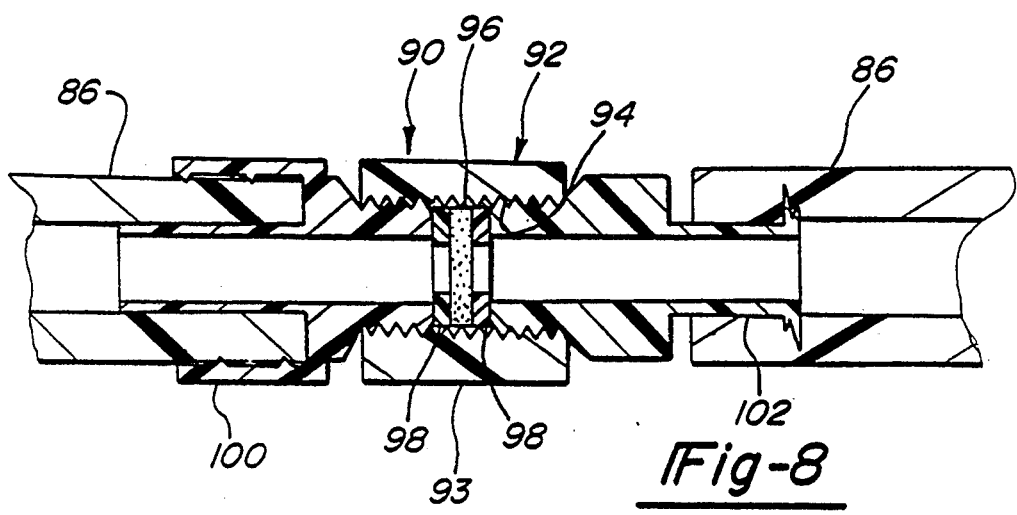
FIG. 8 is a cross-sectional view to the blood stop of FIG. 6 and 7.

Now turning to FIGS. 6 through 8, a device in accordance with another aspect of the present invention is disclosed. FIGS. 6 illustrates a human subject 84 who has previously had an access port implanted of the type described herein or in the related applications. As shown in FIG. 6, access catheter 86 is shown inserted percutaneously through wound 88. Access catheter 86 is shown cutaway and has a portion extending into the patient and another portion outside the patient which would be attached to a therapy device such as a pump, infusion bag, etc. As mentioned previously, in the event that the fluid flow rate into the implanted port through access catheter 86 is not great or stops intermittently as when pulsatile pumps are used, there is a tendency for blood to flow out through access catheter 86 by the action of diffusion, gravity, and the "milking" action discussed previously. The problem of reverse blood diffusion is especially significant in connection with access ports in accordance with this invention as described herein and in the related applications which provide for a large flow rate capacity percutaneous route which is smooth and unobstructed by allowing direct placement of an access catheter into an implanted catheter which enhances the probability that red blood cells can reflex into access catheter 86. In accordance with this invention, blood stop 90 is provided which is shown in FIG. 6 taped to patient 84 and placed in-line with access catheter 86.

The internal components comprising blood stop 90 are shown in FIGS. 7 and 8. Housing 92 has a broad support surface 93 and an angled top surface 95 to facilitate taping to the patient. Within housing passageway 94, filter media element 96 is positioned between a pair of washers 98 which are clamped in position by threaded fittings 100 and 102. Red blood cells can generally be trapped through providing a filter having a capabilities of preventing passage of particles exceeding two microns in size. Accordingly, filter media element 96 preferably has a two micron or smaller blood cell retention characteristic.

In use, any red blood cells which backflow through access catheter 86 are trapped against filter media element 96. When fluid flow occurs into the implanted port, these trapped red blood cells move away from the filter 96 toward the implanted port. Due to the presence of blood stop 90 the patient does not see red cells reverse flowing through access catheter 86.

While the above description constitutes the preferred embodiments of the present invention, it will be appreciated that the invention is susceptible of modification, variation and change without departing from the proper scope and fair meaning of the accompanying claims.

I claim:

1. An access system for enabling the infusion or withdrawal of a fluid to or from a site within the body of a patient, comprising:

an implantable access port permitting the transcutaneous placement of an access catheter, said access port having means for mounting said port within the body of said patient and including a catheter located within the body of the patient for delivering infused fluid, an access catheter placed transcutaneously with a first portion placed within the body of said patient and within said port and a second portion being positioned external to the body of said patient, and a red blood cell trap connected to said second portion of said access catheter and positioned at a location external to the body of said patient, said trap permitting fluids to be infused into said patient and having a filter media element adapted to trap red blood cells migrating from said first portion of said access catheter to said second portion thereby preventing the red blood cells from entering into said second portion of said access catheter.

2. An access system according to claim 1 wherein said filter is designed to trap red blood cells of a size exceeding two microns.

3. An access system according to claim 1 wherein said red blood cell trap includes a fitting to enable in-line placement in said access catheter.

4. An access system according to claim 1 wherein said access port is of a type which permits said access catheter to be placed through said port and into an implanted catheter extending between said port and a site within the body of the patient.

* * * * *